US012697219B2

(12) United States Patent
Smith et al.

(10) Patent No.: US 12,697,219 B2
(45) Date of Patent: Aug. 4, 2026

(54) ELECTRONIC IMPLANTABLE PENILE PROSTHESIS

(71) Applicant: Boston Scientific Scimed, Inc., Maple Grove, MN (US)

(72) Inventors: Noel Smith, Windgap (IE); Eduardo Marcos Larangeira, Cork City (IE); Brian P. Watschke, Minneapolis, MN (US); Daragh Nolan, Youghal (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 857 days.

(21) Appl. No.: 18/068,074

(22) Filed: Dec. 19, 2022

(65) Prior Publication Data

US 2023/0190471 A1     Jun. 22, 2023

Related U.S. Application Data

(60) Provisional application No. 63/265,808, filed on Dec. 21, 2021.

(51) Int. Cl.
*A61F 2/26*     (2006.01)
*A61F 2/48*     (2006.01)

(52) U.S. Cl.
CPC .............. *A61F 2/26* (2013.01); *A61F 2/482* (2021.08); *A61F 2/484* (2021.08); *A61F 2250/0002* (2013.01); *A61F 2250/0013* (2013.01)

(58) Field of Classification Search
CPC .... A61F 2/26; A61F 2220/0008; A61F 2/004; A61F 2/482; A61F 2/484; A61F 2250/0013; F04B 23/04; F04B 23/02; F04B 53/20; A61B 5/6846

USPC .......................................................... 600/40
See application file for complete search history.

(56) References Cited

U.S. PATENT DOCUMENTS

| | | | |
|---|---|---|---|
| 4,584,994 A * | 4/1986 | Bamberger | A61F 2/26 |
| | | | 310/40 MM |
| 8,382,452 B2 | 2/2013 | Richter et al. | |
| 9,410,641 B2 | 8/2016 | Herz et al. | |
| 9,546,651 B2 | 1/2017 | Richter et al. | |
| 11,555,725 B2 | 1/2023 | Wald et al. | |

(Continued)

FOREIGN PATENT DOCUMENTS

| | | | | |
|---|---|---|---|---|
| CN | 101125086 A | * | 2/2008 | |
| CN | 106038031 A | * | 10/2016 | A61F 5/41 |

(Continued)

OTHER PUBLICATIONS

International Search Report and Written Opinion for PCT Application No. PCT/US2022/082040, mailed on Apr. 12, 2023, 16 pages.

(Continued)

*Primary Examiner* — Brian L Casler
(74) *Attorney, Agent, or Firm* — Brake Hughes Bellermann LLP

(57) ABSTRACT

According to an aspect, an inflatable penile prosthesis includes a fluid reservoir configured to hold fluid, an inflatable member, and an electronic pump assembly configured to transfer the fluid between the fluid reservoir and the inflatable member. The electronic pump assembly includes a pump, an active valve disposed in parallel with the pump, and a controller configured to control the pump and the active valve.

19 Claims, 6 Drawing Sheets

(56)                    References Cited

U.S. PATENT DOCUMENTS

| 12,404,849 B2 | 9/2025 | Bussmann et al. |
| 2016/0120649 A1 | 5/2016 | Vaingast et al. |
| 2017/0231738 A1 | 8/2017 | Severson |
| 2019/0350712 A1 | 11/2019 | Weber et al. |
| 2020/0222188 A1 | 7/2020 | Smith et al. |
| 2023/0029038 A1 | 1/2023 | Richter et al. |

FOREIGN PATENT DOCUMENTS

| EP | 0072167 A1 * | 2/1983 | ............... | A61F 2/26 |
| WO | 2019213236 A1 | 11/2019 | | |
| WO | WO-2019222091 A1 * | 11/2019 | ............... | A61F 2/26 |

OTHER PUBLICATIONS

Office Action for CA Application No. 3240085, mailed Dec. 1, 2025, 7 pages.

* cited by examiner

500

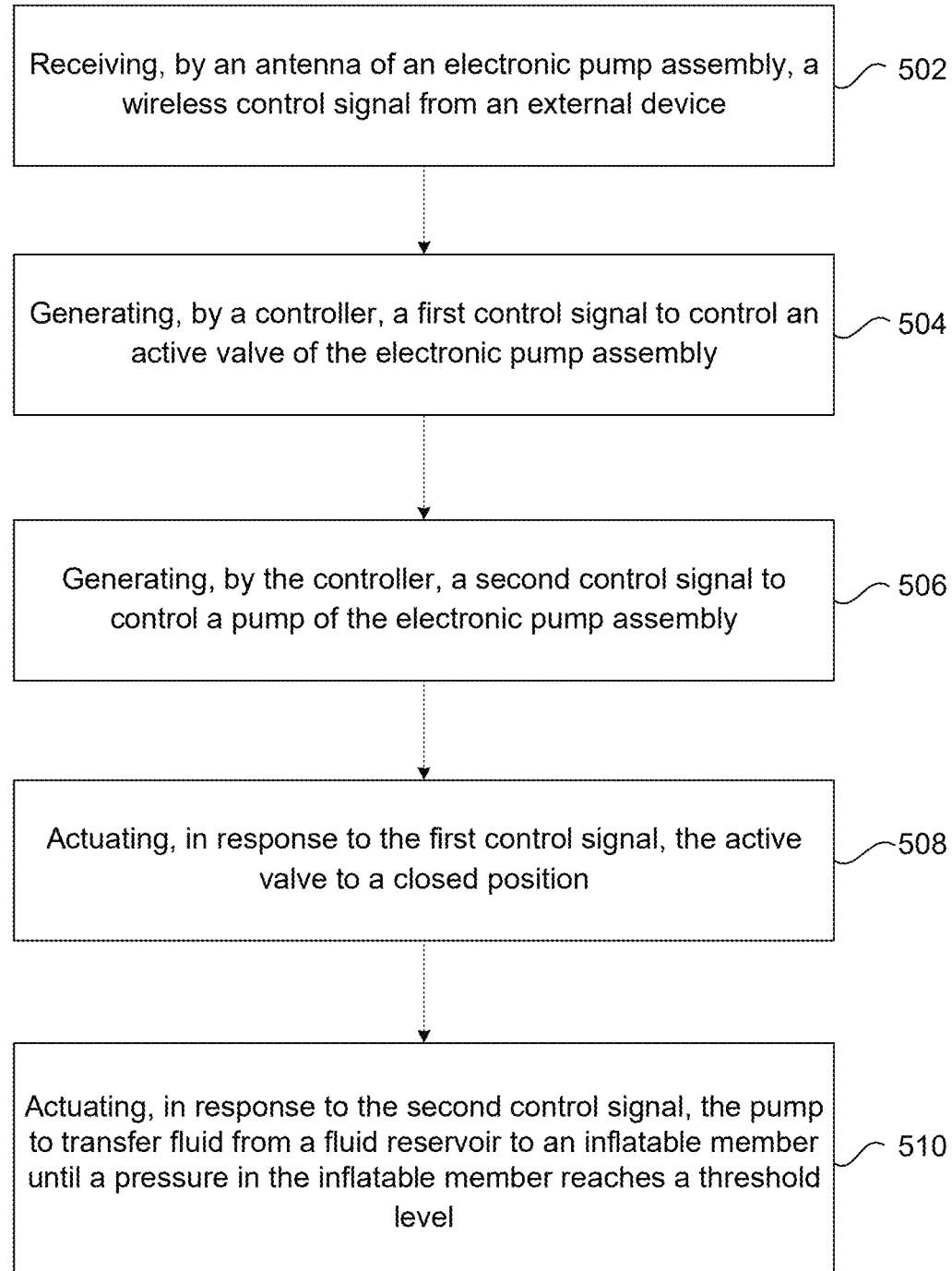

Receiving, by an antenna of an electronic pump assembly, a wireless control signal from an external device ⌐ 502

Generating, by a controller, a first control signal to control an active valve of the electronic pump assembly ⌐ 504

Generating, by the controller, a second control signal to control a pump of the electronic pump assembly ⌐ 506

Actuating, in response to the first control signal, the active valve to a closed position ⌐ 508

Actuating, in response to the second control signal, the pump to transfer fluid from a fluid reservoir to an inflatable member until a pressure in the inflatable member reaches a threshold level ⌐ 510

FIG. 5

ELECTRONIC IMPLANTABLE PENILE PROSTHESIS

CROSS-REFERENCE TO RELATED APPLICATION

This application claims priority to U.S. Provisional Patent Application No. 63/265,808, filed on Dec. 21, 2021, entitled "ELECTRONIC IMPLANTABLE PENILE PROSTHE-SIS", the disclosure of which is incorporated by reference herein in its entirety.

TECHNICAL FIELD

This disclosure relates generally to bodily implants and more specifically to bodily implants, such as an electronic implantable penile prosthesis.

BACKGROUND

One treatment for male erectile dysfunction is the implantation of a penile prosthesis that erects the penis. Some existing penile prosthesis include inflatable cylinders or members that can be inflated or deflated using a pump mechanism. The pump mechanism includes a pump, implantable in the scrotum, that can be manually squeezed by the user to move fluid from a reservoir into the cylinders, creating an erection. For some patients, the manual pumping procedure may be relatively challenging.

SUMMARY

According to an aspect, an inflatable penile prosthesis includes a fluid reservoir configured to hold fluid, an inflatable member, and an electronic pump assembly configured to transfer the fluid between the fluid reservoir and the inflatable member. The electronic pump assembly includes a pump, an active valve disposed in parallel with the pump, and a controller configured to control the pump and the active valve.

According to some aspects, the inflatable penile prosthesis may include one or more of the following features (or any combination thereof). The pump may include an electromagnetic pump. The pump may include a piezoelectric pump. The electronic pump assembly may include an antenna configured to receive a wireless control signal from an external device. The controller is configured to control at least one of the pump or the active valve based on the wireless control signal. In some examples, the pump is a first pump, and the electronic pump assembly includes a second pump. The second pump may be disposed in parallel with the first pump. The second pump may be configured to operate out of phase from the first pump. The second pump may be disposed in series with the first pump. The pump may include one or more passive check valves.

According to an aspect, an inflatable penile prosthesis includes a fluid reservoir configured to hold fluid, an inflatable member, and an electronic pump assembly configured to transfer the fluid between the fluid reservoir and the inflatable member. The electronic pump assembly includes a first pump, a second pump, an active valve, and a controller configured to control the first pump, the second pump, and the active valve.

According to some aspects, the inflatable penile prosthesis may include any of the above/below features (or any combination thereof). The first pump and the active valve may be in parallel with each other. The active valve is configured to transition between an open position in which the fluid flows through the active valve and a closed position in which the fluid is prevented from flowing through the active valve. The electronic pump assembly may include a pressure sensor, where the controller is configured to control at least one of the first pump, the second pump, or the active valve based on a pressure measured by the pressure sensor. The pressure sensor may be connected to the inflatable member. The pressure sensor may be connected to the fluid reservoir. The active valve may be a first active valve, and the electronic pump assembly may include a second active valve. The second active valve may be disposed in series with the first pump. The electronic pump assembly may include a hermetic enclosure, where the hermetic enclosure includes a hermetic fluid chamber. The hermetic fluid chamber includes the first pump, the second pump, and the active valve. The controller being included within the hermetic enclosure but outside of the hermetic fluid chamber.

According to an aspect, a method of operating an inflatable penile prosthesis includes receiving, by an antenna of an electronic pump assembly, a wireless control signal from an external device, generating, by a controller, a first control signal to control an active valve of the electronic pump assembly, generating, by the controller, a second control signal to control a pump of the electronic pump assembly, actuating, in response to the first control signal, the active valve to a closed position, and actuating, in response to the second control signal, the pump to transfer fluid from a fluid reservoir to an inflatable member until a pressure in the inflatable member reaches a threshold level. In some examples, the method includes generating, by the controller, a third control signal to control the active valve and actuating, in response to the third control signal, the active valve to an open position to transfer at least a portion of the fluid from the inflatable member to the fluid reservoir.

BRIEF DESCRIPTION OF THE DRAWINGS

FIG. 5 illustrates a flow chart depicting example operations of an electronic pump assembly according to an aspect.

DETAILED DESCRIPTION

Figure 1:
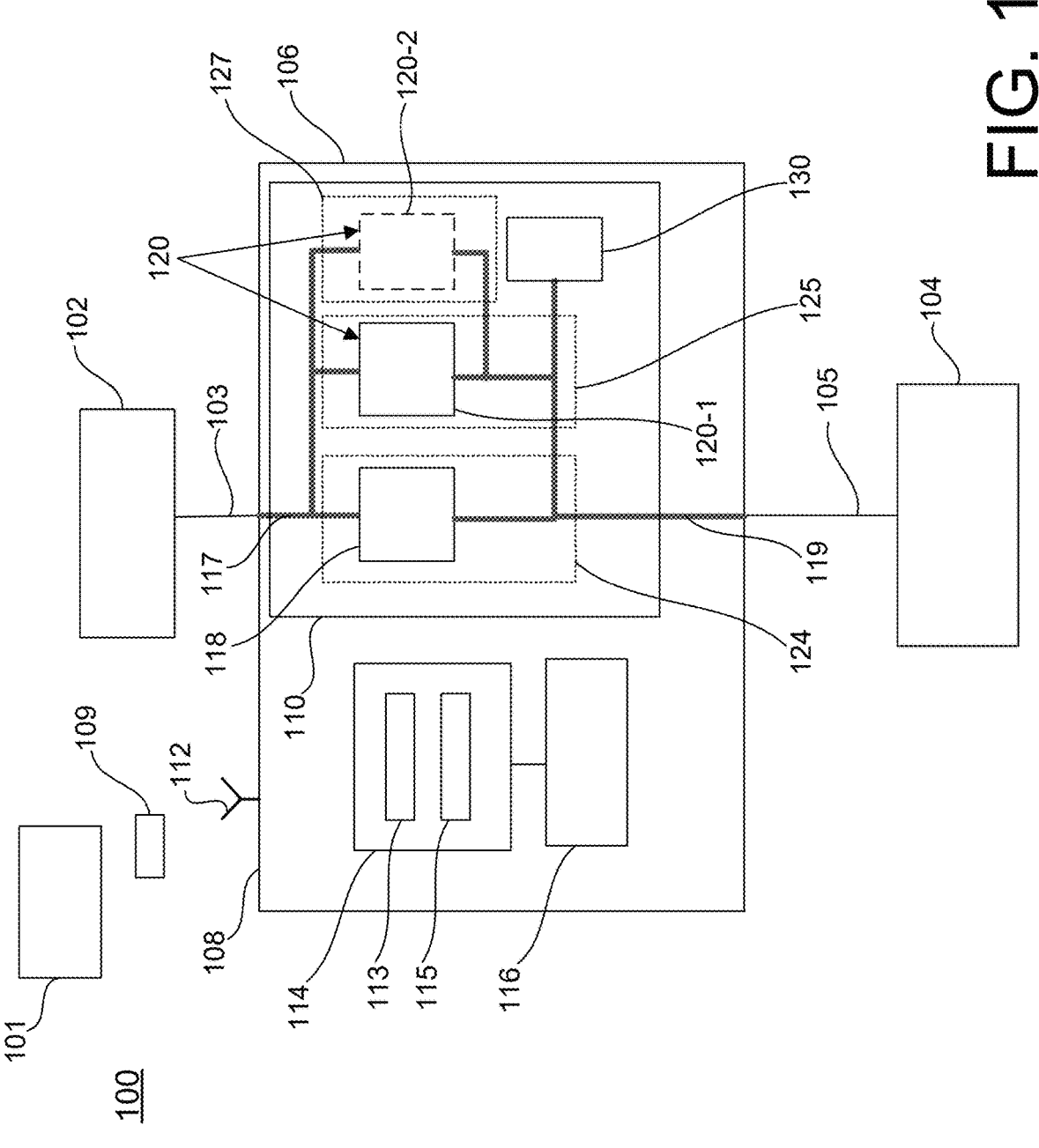
FIG. 1 illustrates an inflatable penile prosthesis having an electronic pump assembly according to an aspect.

This disclosure relates to an inflatable penile prosthesis that includes an electronic pump assembly to transfer fluid between a fluid reservoir and an inflatable member. The electronic pump assembly may wirelessly communicate with an external device (e.g., a computer, a smartphone, tablet, pendant, key fob, etc.) to control the inflatable penile prosthesis (e.g., inflate or deflate the inflatable member, update one or more control parameters). In some examples, the electronic pump assembly includes a primary battery (e.g., a non-rechargeable battery). In some examples, the electronic pump assembly includes a rechargeable battery configured to be recharged by an external charger.

The electronic pump assembly includes one or more pumps (e.g., electronically-controlled pumps such as one or more electromagnetic or Piezoelectric pumps), one or more active valves, and a controller. The controller may actuate the pump(s) and the active valve(s) to control the inflation and deflation of the inflatable member based on control signals transmitted to the pump(s) and the active valve(s). The pump(s) may be unidirectional or bidirectional. In some examples, the electronic pump assembly includes one or more pumps in parallel with an active valve. In some examples, the pump(s) can transfer the fluid to the inflatable member during an inflation cycle, and the active valve may transition to an open position to permit fluid to transfer back to the fluid reservoir during a deflation cycle. The pump(s) may transfer fluid on demand to the inflatable member at a relatively high-pressure rate. In some examples, the electronic pump assembly includes two or more parallel pumps such as a first pump and a second pump, where the first pump and the second pump are configured to operate out of phase from each other, which can increase the efficiency of the pumping operations. In some examples, the use of parallel pumps that operate out of phase from each other may allow the pumps to operate at lower frequencies, which can reduce power and improve battery life. In some examples, the electronic pump assembly may include one or more pumps in series with a pump, which can increase the amount of fluid that can be transferred to the inflatable member during a period of time.

An individual pump may include one or more passive check valves which transition to a closed position in response to positive pressure between the inflatable member and the fluid reservoir. In some examples, an active valve may transition to a closed position to hold (e.g., substantially hold) the pressure in the inflatable member. In some examples, the active valve may transition to an open position to release pressure in the inflatable member and/or allow a flowback to the inflatable member. In some examples, the electronic pump assembly includes a single active valve. In some examples, the electronic pump assembly includes multiple active valves. For example, one or more active valves may be in series with a pump.

The electronic pump assembly may include a pressure sensor configured to sense a pressure of the inflatable penile prosthesis. In some examples, the pressure sensor is coupled to the inflatable member. The pressure sensor may measure the pressure in the inflatable member. The controller may receive the measured pressure from the pressure sensor and automatically control the active valve(s) and/or pump(s) to regulate the pressure in the inflatable member. In some examples, the pressure sensor is connected to the fluid reservoir. In some examples, the pressure sensor may detect intra-abdominal pressure (which can increase during activities such as exercise), and the controller can control the active valve(s) and pump(s) to minimize or prevent accidental inflations.

FIG. 1 illustrates an inflatable penile prosthesis 100 having an electronic pump assembly 106 that can improve inflation and/or deflation operations of the prosthesis's inflatable member 104 according to an aspect. The inflatable penile prosthesis 100 includes a fluid reservoir 102, an inflatable member 104, and an electronic pump assembly 106 configured to transfer fluid between the fluid reservoir 102 and the inflatable member 104. The inflatable member 104 may be implanted into the corpus cavernosum of the user, and the fluid reservoir 102 may be implanted in the abdomen or pelvic cavity of the user (e.g., the fluid reservoir 102 may be implanted in the lower portion of the user's abdominal cavity or the upper portion of the user's pelvic cavity). In some examples, at least a portion of the electronic pump assembly 106 may be implemented in the patient's body.

The inflatable member 104 may be capable of expanding upon the injection of fluid into a cavity of the inflatable member 104. For instance, upon injection of the fluid into the inflatable member 104, the inflatable member 104 may increase its length and/or width, as well as increase its rigidity. In some examples, the inflatable member 104 may include a pair of inflatable cylinders or at least two cylinders, e.g., a first cylinder member and a second cylinder member. The volumetric capacity of the inflatable member 104 may depend on the size of the inflatable cylinders. In some examples, the volume of fluid in each cylinder may vary from about 10 milliliters in smaller cylinders and to about 70 milliliters in larger sizes. In some examples, the first cylinder member may be larger than the second cylinder member. In other examples, the first cylinder member may have the same size as the second cylinder member.

The fluid reservoir 102 may include a container having an internal chamber configured to hold or house fluid that is used to inflate the inflatable member 104. The volumetric capacity of the fluid reservoir 102 may vary depending on the size of the inflatable penile prosthesis 100. In some examples, the volumetric capacity of the fluid reservoir 102 may be 3 to 150 cubic centimeters. In some examples, the fluid reservoir 102 is constructed from the same material as the inflatable member 104. In other examples, the fluid reservoir 102 is constructed from a different material than the inflatable member 104. In some examples, the fluid reservoir 102 contains a larger volume of fluid than the inflatable member 104.

The inflatable penile prosthesis 100 may include a first conduit connector 103 and a second conduit connector 105. Each of the first conduit connector 103 and the second conduit connector 105 may define a lumen configured to transfer the fluid to and from the pump assembly 106. The first conduit connector 103 may be coupled to the electronic pump assembly 106 and the fluid reservoir 102 such that fluid can be transferred between the electronic pump assembly 106 and the fluid reservoir 102 via the first conduit connector 103. For example, the first conduit connector 103 may define a first lumen configured to transfer fluid between the electronic pump assembly 106 and the fluid reservoir 102. The first conduit connector 103 may include a single or multiple tube members for transferring the fluid between the electronic pump assembly 106 and the fluid reservoir 102.

The second conduit connector 105 may be coupled to the pump assembly 106 and the inflatable member 104 such that fluid can be transferred between the electronic pump assembly 106 and the inflatable member 104 via the second conduit connector 105. For example, the second conduit connector 105 may define a second lumen configured to transfer fluid between the electronic pump assembly 106 and the inflatable member 104. The second conduit connector 105 may include a single or multiple tube members for transferring the fluid between the electronic pump assembly 106 and the inflatable member 104. In some examples, the first conduit connector 103 and the second conduit connector 105 may include a silicone rubber material. In some examples, the electronic pump assembly 106 may be directly connected to the fluid reservoir 102.

The electronic pump assembly 106 may automatically transfer fluid between the fluid reservoir 102 and the inflatable member 104 without the user manually operating a pump (e.g., squeezing and releasing a pump bulb). The electronic pump assembly 106 includes one or more pumps 120, one or more active valves 118, a controller 114 configured to control the pump(s) 120 and the active valve 118, and one or more pressure sensors 130. For example, the controller 114 may control the pump(s) 120 to pump fluid between the fluid reservoir 102 and the inflatable member 104. The controller 114 may control the active valve 118 to transition between an open position and a closed position. The pump(s) 120 is configured to transfer fluid (on demand) to the inflatable member 104 at relatively high-pressure (e.g., up to approximately twenty pounds per square inch (PSI)).

The electronic pump assembly 106 may include a battery 116 configured to provide power to the controller 114 and other components on the electronic pump assembly 106. In some examples, the battery 116 is a non-rechargeable battery. In some examples, the battery 116 is a rechargeable battery. In some examples, the electronic pump assembly 106 (or a portion thereof) (or the controller 114) is configured to be connected to an external charger to charge the battery 116. In some examples, the electronic pump assembly 106 may define a charging interface that is configured to connect to the external charger. In some examples, the charging interface includes a universal serial bus (USB) interface configured to receive a USB charger. In some examples, the charging technology may be electromagnetic or Piezoelectric.

The electronic pump assembly 106 may include an antenna 112 configured to wirelessly transmit (and receive) wireless signals 109 from an external device 101. The external device 101 may be any type of component that can communicate with the electronic pump assembly 106. The external device 101 may be a computer, smartphone, tablet, pendant, key fob, etc. A user may use the external device 101 to control the inflatable penile prosthesis 100. In some examples, the user may use the external device 101 to inflate or deflate the inflatable member 104. For example, in response to the user activating an inflation cycle using the external device 101 (e.g., selecting a user control on the external device 101), the external device 101 may transmit a wireless signal 109 to the electronic pump assembly 106 to initiate the inflation cycle (received via the antenna 112), where the controller 114 may control the active valve(s) 118 and the pump(s) 120 to inflate the inflatable member 104 to a target inflation pressure. In some examples, the controller 114 may cause the active valve to a closed position and cause the pump(s) to operate to move fluid from the fluid reservoir 102 to the inflatable member 104.

In some examples, in response to the user activating a deflation cycle using the external device 101 (e.g., selecting a user control on the external device 101), the external device 101 may transmit a wireless signal 109 to the electronic pump assembly 106 to initiate the deflation cycle (received via the antenna 112), where the controller 114 may control the active valve(s) 118 (and, in some examples, the pump(s) 120) to transfer fluid from the inflatable member 104 to the fluid reservoir 102. For example, the controller 114 may control the active valve 118 to move to the open position to allow fluid to transfer from the inflatable member 104 to the fluid reservoir 102. In some examples, the controller 114 may control one or more pumps 120 to further move the fluid from the inflatable member 104 to the fluid reservoir 102 during the deflation cycle. In some examples, during the deflation cycle, fluid is transferred back until the pressure in the inflatable member 104 reaches a partial inflation pressure. In some examples, the controller 114 may automatically determine to initiate a deflation cycle, which causes the controller 114 to control the active valve(s) 118

(and, in some examples, the pump(s) 120) to transfer fluid back to the fluid reservoir 102.

The controller 114 may be any type of controller configured to control operations of the pump(s) 120 and the active valve(s) 118. In some examples, the controller 114 is a microcontroller. In some examples, the controller 114 includes one or more drivers configured to drive the pump(s) 120 and the active valve(s) 118. In some examples, the driver(s) are components separate from the controller 114. The controller 114 may be communicatively coupled to the active valve(s) 118, the pump(s) 120, and the pressure sensor(s) 130. In some examples, the controller 114 is connected to the active valve(s) 118, the pump(s) 120, and the pressure sensor(s) 130 via wired data lines. The controller 114 may include a processor 113 and a memory device 115. The processor 113 may be formed in a substrate configured to execute one or more machine executable instructions or pieces of software, firmware, or a combination thereof. The processor 113 can be semiconductor-based—that is, the processors can include semiconductor material that can perform digital logic. The memory device 115 may store information in a format that can be read and/or executed by the processor 113. The memory device 115 may store executable instructions that when executed by the processor 113 cause the processor 113 to perform certain operations discussed herein. The controller 114 may receive data via the pressure sensor(s) 130 and/or the external device 101 and control the active valve(s) 118 and/or the pump(s) 120 by transmitting control signals to the active valve(s) 118 and/or the pump(s) 120.

The memory device 115 may store control parameters that can be set or modified by the user and/or physician using the external device 101. In some examples, the control parameters may include the target inflation pressure and/or the partial inflation pressure. In some examples, the target inflation pressure is a maximum (or desired) pressure allowable in the inflatable member 104. In some examples, the partial inflation pressure is a pressure threshold that can more closely mimic the natural experience and/or personal comfort of the user. A user or physician may update the control parameters using the external device 101, which can be communicated to the controller 114 via the antenna 112 and then updated in the memory device 115.

The external device 101 may communicate with the electronic pump assembly 106 over a network. In some examples, the network includes a short-range wireless network such as near field communication (NFC), Bluetooth, or infrared communication. In some examples, the network may include the Internet (e.g., Wi-Fi) and/or other types of data networks, such as a local area network (LAN), a wide area network (WAN), a cellular network, satellite network, or other types of data networks.

In some examples, the electronic pump assembly 106 includes a single pump 120 such as a pump 120-1. The pump 120-1 may be disposed in parallel with the active valve 118. In some examples, the electronic pump assembly 106 includes multiple pumps 120. For example, the pumps 120 include pump 120-1 and pump 120-2. In some examples, the pump 120-1 is disposed in a fluid passageway 125 that is used to fill the inflatable member 104 (e.g., during the inflation cycle). In some examples, the pump 120-2 is disposed in a fluid passageway 127 that is used to fill the inflatable member 104 (e.g., during the inflation cycle). In some examples, the pump 120-2 is disposed in parallel with the pump 120-1. The pump 120-1 may transfer fluid according to a first flow rate, and the pump 120-1 may transfer fluid according to a second flow rate. In some examples, the first flow rate is substantially the same as the second flow rate. In some examples, the first flow rate is different from the second flow rate.

In some examples, the pumps 120 may include more than two pumps 120 such as three, four, five, six, or greater than six pumps 120. For example, the pumps 120 may include a third pump in parallel with the pump 120-2, a fourth pump in parallel with the third pump, and so forth. In some examples, the pumps 120 may include one or more pumps 120 in series with one or more other pumps 120. For example, one or more pumps 120 may be in series with the pump 120-1. In some examples, one or more pumps 120 may be in series with the pump 120-2.

Each pump 120 is an electronically-controlled pump. Each pump 120 may be electronically-controlled by the controller 114. For example, each pump 120 may be connected to the controller 114 and may receive a signal to actuate a respective pump 120. A pump 120 may be unidirectional in which the pump 120 can transfer fluid from the fluid reservoir 102 to the inflatable member 104 (or from the inflatable member 104 to the fluid reservoir 102). In some examples, a pump 120 is bidirectional in which the pump 120 can transfer fluid from the fluid reservoir 102 to the inflatable member 104 and from the inflatable member 104 to the fluid reservoir 102. In some examples, the pumps 120 are either unidirectional or bidirectional. In some examples, the pumps 120 include a combination of one or more unidirectional pumps and one or more bidirectional pumps.

In some examples, the pump 120 is an electromagnetic pump that moves the fluid between the fluid reservoir 102 and the inflatable member 104 using electromagnetism. With respect to an electromagnetic pump, a magnetic fluid is set at angles to the direction the fluid moves in, and a current is passed through it.

In some examples, the pump 120 is a piezoelectric pump. In some examples, a piezoelectric pump may be a diaphragm micropump that uses actuation of a diaphragm to drive a fluid. In some examples, a piezoelectric pump may include one or more piezo pumps (e.g., piezo elements), which may be implemented by a substrate layer (e.g., a single substrate layer) of high-voltage piezo elements or may be implemented by multiple substrate layers (e.g., stacked substrate layers) of low-voltage piezo elements. In some examples, the pump 120 includes a plurality of micro-pumps (e.g., piezoelectrically-driven micro-pumps) disposed on one or more substrates (e.g., wafer(s)). In some examples, the micro-pumps include a silicon-based material. In some examples, the micro-pumps include a metal (e.g., steel) based material. In some examples, the pump 120 is non-mechanical (e.g., without moving parts).

In some examples, in the case of multiple pumps 120, each pump 120 may be a pump of the same type (e.g., all pumps 120 are electromagnetic pumps or all pumps 120 are piezoelectric pumps). In some examples, one or more pumps 120 are different from one or more other pumps 120. For example, pumps 120 may include different types of piezoelectric pumps or the pumps 120 may include different types of electromagnetic pumps. The pump 120-1 may be a piezoelectric pump having a first number of micro-pumps, and the pump 120-2 may be a piezoelectric pump having a second number of micro-pumps (where the second number is different from the first number). The pump 120-1 may be an electromagnetic pump, and the pump 120-2 may be a piezoelectric pump.

A pump 120 may include one or more passive check valves. The passive check valve(s) may assist with maintaining pressure in the inflatable member 104. In some examples, a pump 120 may include a single passive check valve. In some examples, the pump 120 may include multiple passive check valves such as two passive check values or more than two passive check valves. The passive check valve(s) of a respective pump 120 may not be directly controlled by the controller 114, but rather based on the pressure between the inflatable member 104 and the fluid reservoir 102. The passive check valve(s) may transition between an open position (in which fluid is permitted to flow through the passive check valve(s)) and a closed position (in which fluid is prevented from flowing through the passive check valve(s)). In some examples, the passive check valve(s) transitions to the closed position in response to positive pressure between the inflatable member 104 and the fluid reservoir 102. In some examples, the passive check valve(s) transition to the open position in response to negative pressure between the inflatable member 104 and the fluid reservoir 102.

In some examples, the use of two parallel pumps (e.g., pump 120-1, pump 120-2) (or more than two parallel pumps 120) may increase the amount of fluid that can be transferred to the inflatable member 104. In some examples, the pumps 120 may operate out of phase from each other in order to increase the efficiency of the electronic pump assembly 106. Two parallel pumps (e.g., pump 120-1, pump 120-2) operating at out of phase (e.g., 180 degrees of out of phase) from each other may allow the output pressure of the pump 120-1 to improve the valve closure of the pump 120-2, thereby improving the overall performance (and vice versa). The use of parallel pumps 120 operating out of phase from each other may allow the pumps 120 to operate at lower frequencies, which can reduce power (thereby extending battery life). Furthermore, a smoother flow rate may also be achieved resulting in less vibration and an improved patient experience. As indicated above, one or more pumps 120 may be in series with one or more parallel pumps 120. For example, an additional pump 120 may be in series with the pump 120-1, and/or an additional pump 120 may be in series with the pump 120-2. Serial pump operation may enable doubling of the pressure when two similar-performing pumps 120 are utilized. In some examples, two or more serially-disposed pumps 120 may be operated at the same phase.

Out of phase may refer to two or more control signals whose phase relationship with each other is such that one control signal is at its positive peak while the other control signal is at (or near) its negative peak. The pump 120-1 may operate according to a first control signal (generated by the controller 114), and the pump 120-2 may operate according to a second control signal (generated by the controller 114). The first and second control signals may control the pump 120-1 and the pump 120-2, respectively, to operate out of phase from one another. Each of the first control signal and the second control signal may define a series of activation states, e.g., a first state and a second state. For example, each of the first control signal and the second control signal may include a waveform having a series of first states (one of high states or low states) and second states (one of low states or high states). The first state may indicate that a diaphragm element moves in a first direction, and the second state may indicate that the diaphragm element moves in a second direction (opposite to the first direction). The first signal may indicate the first state during a first period of time, followed by the second state during a second period of time, followed by the first state during a third period of time, followed by the second state during a fourth period of time, and so forth. The second signal may indicate the second state during the first period of time, followed by the first state during the second period time, the second state during the third period of time, the first state during the fourth period of time, and so forth.

The active valve 118 may be an electronically-controlled valve. The active valve 118 may be electronically-controlled by the controller 114. For example, the active valve 118 may be connected to the controller 114 and may receive a signal to transition the active valve 118 between an open position in which the fluid flows through the active valve 118 and a closed position in which the fluid is prevented from flowing through the active valve 118. In some examples, the active valve 118 is disposed in a fluid passageway 124 that is used to empty the inflatable member 104 (e.g., in the deflation cycle). In some examples, the active valve 118 may transition to the closed position to hold (e.g., substantially hold) the pressure in the inflatable member 104. In some examples, the active valve 118 may transition to the open position to transfer fluid back to the fluid reservoir 102, release pressure in the inflatable member 104 and/or allow a flow back to the inflatable member 104. In some examples, the active valve 118 may be used to hold (e.g., substantially hold) the partial inflation pressure.

In some examples, the electronic pump assembly 106 includes a single active valve 118. In some examples, the electronic pump assembly 106 includes multiple active valves 118. In some examples, one or more additional active valves 118 may be in series with the pump 120-1 and/or the pump 120-2. In some examples, an additional active valve 118 (e.g., a series active valve 118) may be disposed in a fluid pathway portion 117 that is connected to the fluid reservoir 102. In some examples, an additional active valve 118 (e.g., a series active valve 118) may be disposed in a fluid pathway portion 119 that is connected to the inflatable member 104. These additional active valves 118 may reduce leakage when at maximum inflation pressure or at partial inflation pressure.

The electronic pump assembly 106 may include one or more pressure sensors 130 configured to sense a pressure of the inflatable penile prosthesis 100. In some examples, the electronic pump assembly 106 includes a single pressure sensor 130. In some examples, the electronic pump assembly 106 may include multiple pressure sensors 130. For example, the pressure sensors 130 may include a pressure sensor 130 configured to measure the pressure of the inflatable member and/or a pressure sensor 130 configured to measure the pressure of the fluid reservoir 102. In some examples, the electronic pump assembly 106 may include additional pressure sensors 130, which can be located at various positions in the electronic pump assembly 106. For example, a pressure sensor 130 may be disposed between active valves 118. In some examples, a pressure sensor 130 may be disposed between two pumps 120 connected in series. In some examples, a pressure sensor 130 may be disposed between two pumps 120 connected in parallel. In some examples, a pressure sensor 130 may be disposed between an active valve 118 and a pump 120. The pressure sensor(s) 130 are communicatively coupled to the controller 114 such that the controller 114 can receive signals from the pressure sensor 130. In some examples, a pressure sensor 130 is configured to sense the amount of fluid transferred to the inflatable member 104 and send one or more signals to the controller 114 that indicate the amount of fluid that has been transferred.

In some examples, the pressure sensor 130 is disposed between the pump(s) 120 and the inflatable member 104, as shown in FIG. 1. The pressure sensor 130 may measure the pressure in the inflatable member 104. The controller 114 may receive the measured pressure from the pressure sensor 130 and automatically control the active valve(s) 118 and/or pump(s) 120 to regulate the pressure. For example, if the measured pressure is greater than the target inflation pressure, the controller 114 may transition the active valve 118 to the open position (to allow fluid to transfer back to fluid reservoir 102), when the measured pressure achieves the target inflation pressure, the controller 114 may transition the active valve 118 to the closed position to maintain the pressure in the inflatable member 104. In some examples, a pressure sensor 130 is disposed between the pump(s) 120 and the fluid reservoir 102. In some examples, the pressure sensor 130 may detect intra-abdominal pressure (which can increase during activities such as exercise), and the controller 114 can control the active valve(s) 118 and the pump(s) to minimize or prevent accidental inflations.

In some examples, a pressure sensor 130 is included within the inflatable member 104. In some examples, the pressure sensor 130 is integrated into a wall of a cylinder of the inflatable member 104. In some examples, when the pressure sensor 130 is integrated in the wall of the cylinder, the pressure sensor 130 may monitor the condition of the cylinder material, and the pressure sensor 130 can monitor the changing of the cylinder material to a point where the cylinder might have to be replaced. In this case, the controller 114 may send information, over a network, to an external device 101 on a regular basis for potential check-ups.

In some examples, the pressure sensor 130 is configured to sense the pressure level and send one or more signals to the controller 114 that indicate the pressure level in the inflatable member 104, the fluid reservoir 102, and/or other locations of the inflatable penile prosthesis 100. In some examples, the pressure sensor 130 is configured to monitor the flow rate (e.g., the flow rate in both directions). The controller 114 may control the activation (and deactivation) of the pump(s) 120 and/or the active valve(s) 118 based on the signals received from the pressure sensor(s) 130.

In some examples, the electronic pump assembly 106 includes a hermetic enclosure 108 that encloses the components of the electronic pump assembly 106. A hermetic enclosure 108 may be an air-tight (or substantially air-tight) container. The hermetic enclosure 108 may include one or more metal-based materials. In some examples, the hermetic enclosure 108 is a Titanium container. In some examples, the only material in contact with the patient is Titanium. In some examples, the hermetic enclosure 108 includes one or more non-metal-based materials (e.g., ceramic). In some examples, a portion of the hermetic enclosure 108 is a metal-based material and a portion of the hermetic enclosure 108 is a non-metal-based material. In some examples, the hermetic enclosure 108 defines a feedthrough (e.g., a hermetic feedthrough, an electrical feedthrough, a feedthrough connector, etc.) to receive/transmit wireless signals from/to the external device 101. In some examples, the feedthrough includes a metal-based material and an insulator-based material (e.g., ceramic).

In some examples, the electronic pump assembly 106 includes a hermetic fluid chamber 110 disposed inside of the hermetic enclosure 108. The hermetic fluid chamber 110 may be a separate air-tight (or substantially air-tight) container that is within the hermetic enclosure 108. The hermetic fluid chamber 110 may include one or more metal-based materials. In some examples, the hermetic fluid chamber 110 is a Titanium container. The hermetic fluid chamber 110 may isolate the fluid from the electronics (e.g., the controller 114, the battery 116, etc.). In other words, the electronics section may be isolated (e.g., completely iso-lated) from the fluid via the hermetic fluid chamber 110. The hermetic fluid chamber 110 may be fluidly connected to the fluid reservoir 102 and the inflatable member 104. The hermetic fluid chamber 110 may include the active valve(s) 118, the pump(s) 120, and the pressure sensor(s) 130. In some examples, the hermetic fluid chamber 110 defines a feedthrough (e.g., a hermetic feedthrough, an electrical feedthrough, a feedthrough connector, etc.) to the controller 114 to receive/transmit signals from/to the controller 114. In some examples, the hermetic fluid chamber 110 disposed within the hermetic enclosure 108 creates a double hermetic system. In some examples, the electronic pump assembly 106 includes only one hermetic enclosure (e.g., the hermetic enclosure 108).

Figure 2A:
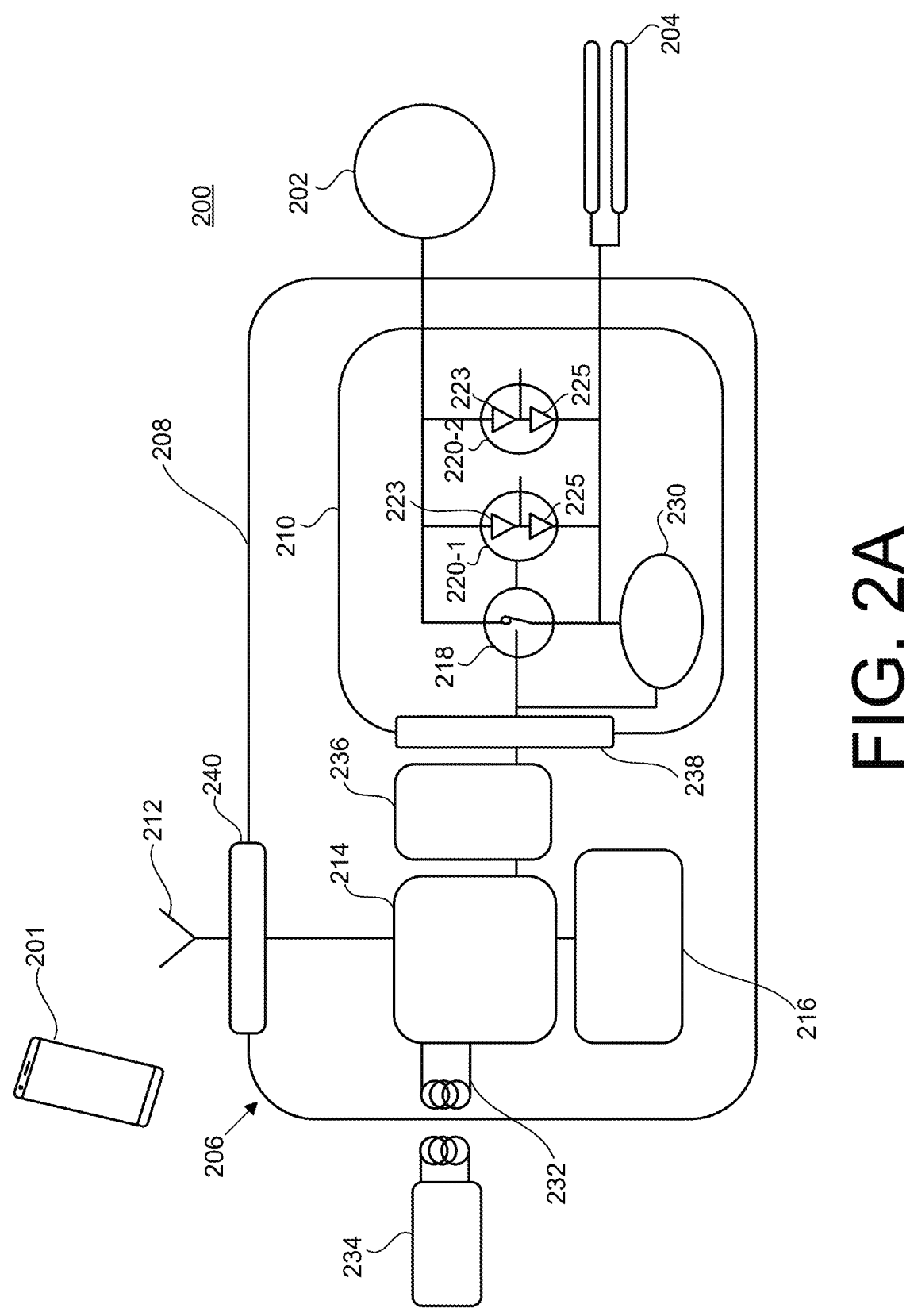
FIG. 2A illustrates an inflatable penile prosthesis having an electronic pump assembly according to another aspect.
Figure 2B:
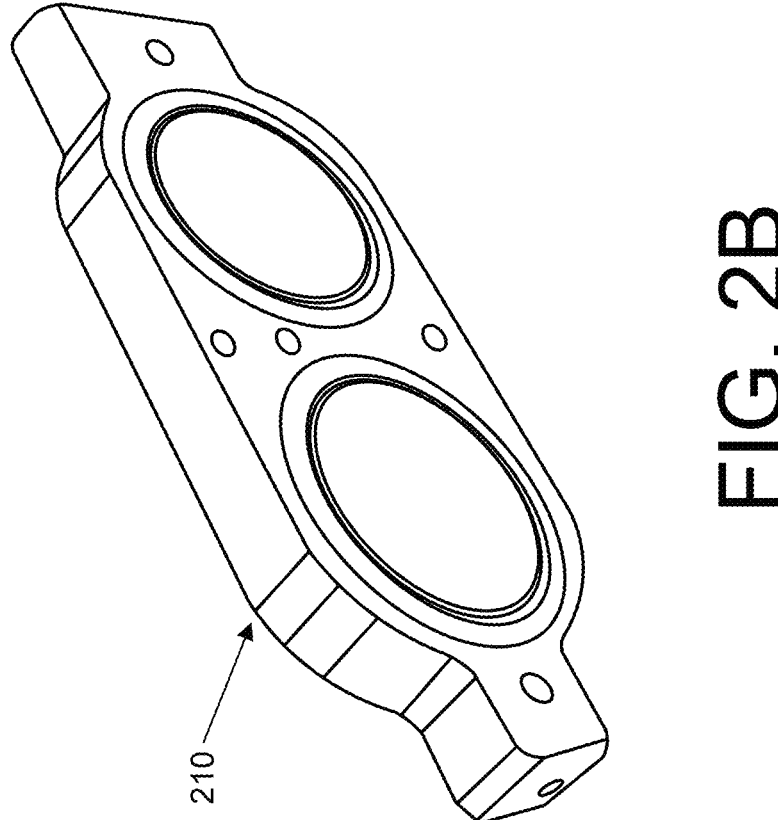
FIG. 2B illustrates an example of a hermetic fluid chamber of the electronic pump assembly according to an aspect.

FIG. 2A illustrates an inflatable penile prosthesis 200 having an electronic pump assembly 206 according to an aspect. FIG. 2B illustrates an example of a hermetic fluid chamber 210 of the electronic pump assembly 206 according to an aspect. The inflatable penile prosthesis 200 of FIGS. 2A and 2B may be an example of the inflatable penile prosthesis 100 of FIG. 1 and may include any of the details discussed with reference to FIG. 1.

The inflatable penile prosthesis 200 includes a fluid reservoir 202, an inflatable member 204, and an electronic pump assembly 206 configured to transfer fluid between the fluid reservoir 202 and the inflatable member 204. The electronic pump assembly 206 may automatically transfer fluid between the fluid reservoir 202 and the inflatable member 204 without the user manually operating a pump (e.g., squeezing and releasing a pump bulb). The electronic pump assembly 206 includes a hermetic enclosure 208 that encloses the components of the electronic pump assembly 206. A hermetic enclosure 208 may be an air-tight (or substantially air-tight) metal-based container. In some examples, the hermetic enclosure 208 is a Titanium con-tainer. In some examples, the only material in contact with the patient is Titanium.

The electronic pump assembly 206 includes an active valve 218, a pump 220-1, a pump 220-2, a pressure sensor 230, a driver 236 to drive the active valve 218, the pump 220-1, and the pump 220-2, and a battery 216 to power the controller 214 (and other electrical components). In some examples, the battery 216 is a non-rechargeable battery. In some examples, the battery 216 is a rechargeable battery. In some examples, the electronic pump assembly 206 (or a portion thereof) is configured to be connected to an external charger 234 to charge the battery 216. In some examples, the controller 214 may include a charging interface 232 that is configured to connect to the external charger 234. In some examples, the charging technology may be electromagnetic or Piezoelectric.

The electronic pump assembly 206 may include an antenna 212 configured to wirelessly transmit (and receive) wireless signals from an external device 201. In some examples, the external device 201 is a smartphone, as shown in FIG. 2A. However, the external device 201 may be any type of component that can communicate with the electronic pump assembly 206 such as a computer (laptop or desktop), a tablet, a pendant, a key fob, etc. A user may use the external device 201 to control the inflatable penile prosthesis 200. The electronic pump assembly 206 may include a feedthrough 240 through the hermetic enclosure 208 to receive/transmit wireless signal via the antenna 212. For example, the antenna 212 may be connected (e.g., via one or more wired connection lines) to the controller 214 in which the wired connection line(s) extend through the feedthrough

240. The external device 201 may communicate with the controller 214 over a network. In some examples, the network includes a short-range wireless network such as near field communication (NFC), Bluetooth, or infrared communication. In some examples, the network may include the Internet (e.g., Wi-Fi) and/or other types of data networks, such as a local area network (LAN), a wide area network (WAN), a cellular network, satellite network, or other types of data networks.

The controller 214 may be any type of controller config-ured to control operations of the pump 220-1, the pump 220-2, and the active valve 218. In some examples, the electronic pump assembly 206 includes one or more drivers 236 configured to drive the pump 220-1, the pump 220-2, and the active valve 218 based on control signals generated by the controller 214.

The electronic pump assembly 206 may include a her-metic fluid chamber 210 disposed inside of the hermetic enclosure 208. The hermetic fluid chamber 210 may be a separate air-tight (or substantially air-tight) container that is within the hermetic enclosure 208. The hermetic fluid cham-ber 210 may include one or more metal-based materials. In some examples, the hermetic fluid chamber 210 is a Tita-nium container. The hermetic fluid chamber 210 may isolate the fluid from the electronics (e.g., the controller 214, the driver(s) 236, the battery 216, etc.). In other words, the electronics section may be completely isolated from the fluid via the hermetic fluid chamber 210. The hermetic fluid chamber 210 may be fluidly connected to the fluid reservoir 202 and the inflatable member 204. The hermetic fluid chamber 210 may include the active valve 218, the pump 220-1, the pump 220-1, and the pressure sensor 230.

The hermetic fluid chamber 210 defines a feedthrough 238 (e.g., a hermetic feedthrough, an electrical feedthrough, a feedthrough connector, etc.) to the driver(s) 236 and/or the controller 214 to exchange signals between the controller 214, the driver 236, and the components included within the hermetic fluid chamber 210 such as the active valve 218, the pump 220-1, the pump 220-2, and the pressure sensor 230. In some examples, the driver(s) 236 (and/or the controller 214) are connected to the active valve 218, the pump 220-1, the pump 220-2, and the pressure sensor 230 via one or more wired connection lines, where the wired connection lines extend through the feedthrough 238. In some examples, the hermetic fluid chamber 210 disposed within the hermetic enclosure 208 creates a double hermetic system. In some examples, the electronic pump assembly 206 includes only one hermetic enclosure (e.g., the hermetic enclosure 208).

The pump 220-1 may include an inlet and an outlet. The inlet of the pump 220-1 may be fluidly connected to the fluid reservoir 202, and the outlet of the pump 220-1 may be fluidly connected to the inflatable member 204. The pump 220-1 may include an inlet and an outlet. The inlet of the pump 220-2 may be fluidly connected to the fluid reservoir 202, and the outlet of the pump 220-2 may be fluidly connected to the inflatable member 204. The active valve 218 may include an inlet and an outlet. The inlet of the active valve 218 may be fluidly connected to the inflatable member 204 and the outlet of the active valve 218 may be fluidly connected to the fluid reservoir 202.

The pump 220-1 and the pump 220-2 are electronically-controlled pumps. The pump 220-1 and the pump 220-2 may be electronically-controlled by the controller 214. For example, each of the pump 220-1 and the pump 220-2 may be connected to the driver(s) 236 and/or the controller 214 to receive control (driving) signals. In some examples, the pump 220-1 and the pump 220-2 are unidirectional in which the pump 220-1 and the pump 220-2 can transfer fluid from the fluid reservoir 202 to the inflatable member 204. However, in some examples, the pump 220-1 and the pump 220-2 are bidirectional. In some examples, the pump 220-1 or the pump 220-2 is an electromagnetic pump that moves the fluid between the fluid reservoir 202 and the inflatable member 204 using electromagnetism. With respect to an electromagnetic pump, a magnetic fluid is set at angles to the direction the fluid moves in, and a current is passed through it.

In some examples, the pump 220-1 or the pump 220-2 is a piezoelectric pump. In some examples, a piezoelectric pump may be a diaphragm micropump that uses actuation of a diaphragm to drive a fluid. In some examples, a piezo-electric pump may include one or more piezo pumps (e.g., piezo elements), which may be implemented by a substrate layer (e.g., a single substrate layer) of high-voltage piezo elements or may be implemented by multiple substrate layers (e.g., stacked substrate layers) of low-voltage piezo elements. In some examples, the pump 220-1 or the pump 220-2 includes a plurality of micro-pumps (e.g., piezoelectrically-driven micro-pumps) disposed on one or more substrates (e.g., wafer(s)). In some examples, the micro-pumps include a silicon-based material. In some examples, the micro-pumps include a metal (e.g., steel) based material. In some examples, the pump 220-1 or the pump 220-2 is non-mechanical (e.g., without moving parts).

The pump 220-1 or the pump 220-2 may include a passive check valve 223 and a passive check valve 225. The passive check valve 223 and the passive check valve 225 may assist with maintaining pressure in the inflatable member 204. The pump 220-1 may be disposed in parallel with the active valve 218. The pump 220-2 may be disposed in parallel with the pump 220-1. In some examples, the use of two parallel pumps (e.g., pump 220-1, pump 220-2) may increase the amount of fluid that can be transferred to the inflatable member 204. In some examples, the pump 220-1 and the pump 220-1 may operate out of phase from each other in order to increase the efficiency of the electronic pump assembly 206. In some examples, two parallel pumps (e.g., pump 220-1, pump 220-2) operating out of phase (e.g., 180 degrees of out of phase) from each other may allow the output pressure of the pump 220-1 to improve the valve closure of the pump 220-2, thereby improving the overall performance (and vice versa). In some examples, the use of parallel pumps (e.g., pump 220-1, pump 220-2) operating out of phase from each other may allow the pump 220-1 and the pump 220-2 to operate at lower frequencies, which can reduce power (thereby extending battery life). Furthermore, a smoother flow rate may also be achieved resulting in less vibration and an improved patient experience.

The active valve 218 may be an electronically-controlled valve. The active valve 218 may be electronically-controlled by the controller 214. For example, the active valve 218 may be connected to the driver(s) 236 (and/or the controller 214) and may receive a signal to transition the active valve 218 between an open position in which the fluid flows through the active valve 218 and a closed position in which the fluid is prevented from flowing through the active valve 218. In some examples, the active valve 218 may transition to the closed position to hold (e.g., substantially hold) the pressure in the inflatable member 204. In some examples, the active valve 218 may transition to the open position to transfer fluid back to the fluid reservoir 202, release pressure in the inflatable member 204 and/or allow a flow back to the inflatable member 204. In some examples, the active valve 218 may be used to hold (e.g., substantially hold) the partial inflation pressure.

The pressure sensor 230 is configured to measure the pressure of the inflatable member 204. The pressure sensor 230 may be coupled to a portion of the fluid passageway connected to the inflatable member 204. In some examples, the pressure sensor 230 may be coupled to a portion of the fluid passageway between the active valve 218 and the inflatable member 204. In some examples, the pressure sensor 230 may be coupled to a portion of the fluid passageway between the pump 220-1 and the inflatable member 204. In some examples, the pressure sensor 230 may be coupled to a portion of the fluid passageway between the pump 220-2 and the inflatable member 204. The pressure sensor 230 is communicatively coupled to the controller 214 such that the controller 214 can receive signals from the pressure sensor 230. The controller 214 may receive the measured pressure from the pressure sensor 230 and automatically control the active valve 218, the pump 220-1, and the pump 220-2. For example, if the measured pressure is less than the target inflation pressure, the controller 214 may actuate the pump 220-1 and the pump 220-2 to pump additional fluid to the inflatable member 204.

Figure 3:
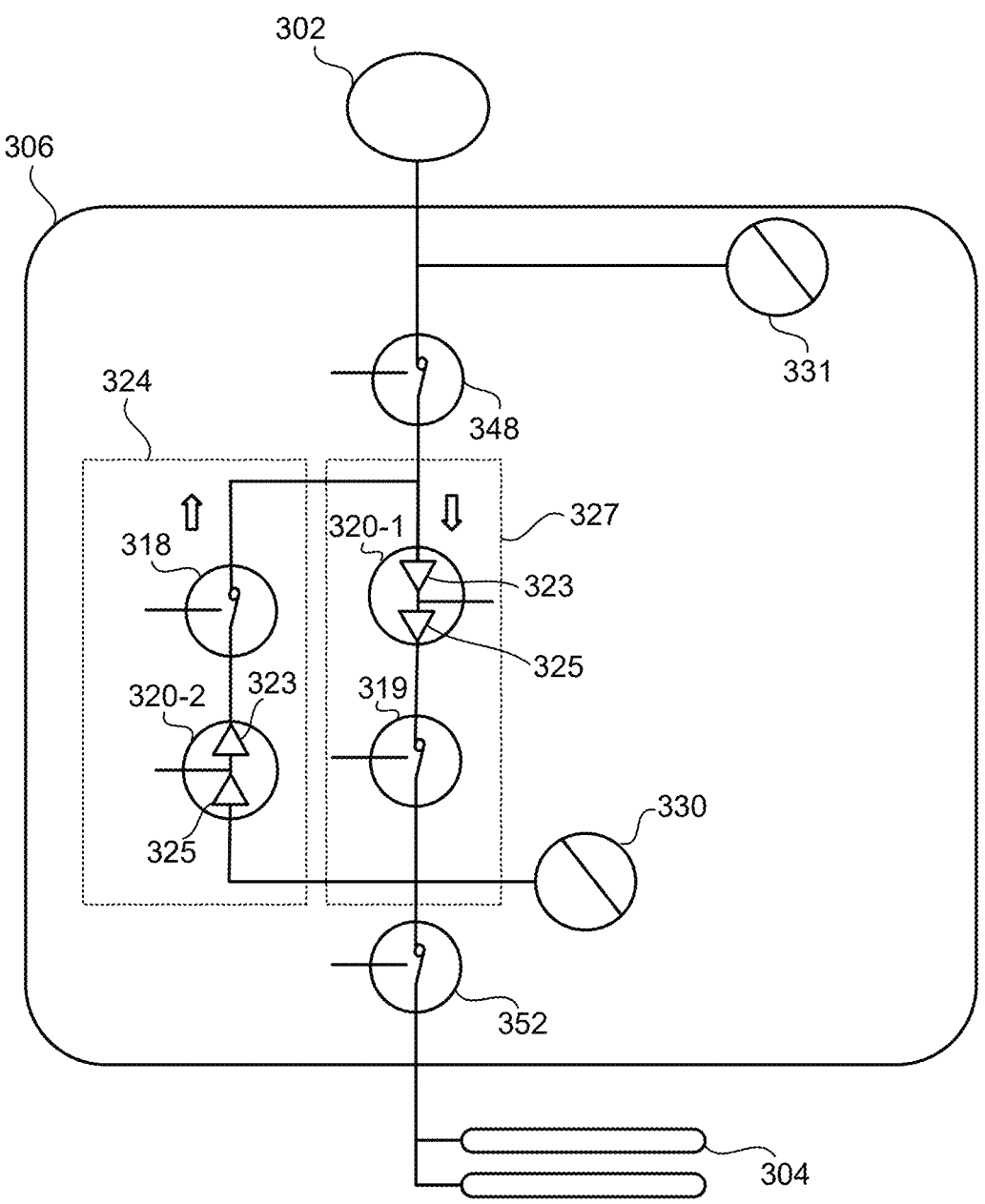
FIG. 3 illustrates an example of an electronic pump assembly according to an aspect.

FIG. 3 illustrates an example of a portion of an electronic pump assembly 306 according to an aspect. The electronic pump assembly 306 may be an example of the electronic pump assembly 106 of FIG. 1 and/or the electronic pump assembly 206 of FIGS. 2A and 2B and may include any of the details discussed with reference to the inflatable penile prosthesis 100 of FIG. 1 and/or the inflatable penile prosthesis 200 of FIGS. 2A and 2B.

The electronic pump assembly 306 is configured to transfer fluid between the fluid reservoir 302 and the inflatable member 304. The electronic pump assembly 306 may automatically transfer fluid between the fluid reservoir 302 and the inflatable member 304 without the user manually operating a pump (e.g., squeezing and releasing a pump bulb).

The electronic pump assembly 306 includes a pump 320-1 disposed within a fluid passageway 327 (e.g., a fill passageway), and an active valve 318 disposed within a fluid passageway 324 (e.g., an empty passageway). The pump 320-1 may be an electromagnetic pump or a Piezoelectric pump. The pump 320-1 may include a passive check valve 323 and a passive check valve 325. The fluid passageway 327 may be a fluid branch that is separate (and parallel) to the fluid passageway 324. The fluid passageway 327 is the passageway that transfers fluid from the fluid reservoir 302 to the inflatable member 304. The fluid passageway 324 is the passageway that transfers fluid from the inflatable member 304 to the fluid reservoir 302. The pump 320-1 is disposed in parallel with the active valve 318.

In some examples, the electronic pump assembly 306 may include an active valve 319 in series with the pump 320-1 (e.g., the pump 320-1 and the active valve 319 are disposed within the fluid passageway 327). In some examples, the electronic pump assembly 306 may include a pump 320-2 in series with the active valve 318 (e.g., the pump 320-2 and the active valve 318 are disposed in the fluid passageway 324). The pump 320-2 may be an electromagnetic pump or a Piezoelectric pump. The pump 320-2 may include a passive check valve 323 and a passive check valve 325. In some examples, the electronic pump assembly 306 includes an active valve 348 that is fluidly connected to the fluid reservoir 302. The active valve 348 may be in series with either the active valve 318 (and the pump 320-2) or the pump 320-1 (and the active valve 319). In some examples, the electronic pump assembly 306 includes an active valve 352 that is fluidly connected to the inflatable member 304.

The active valve 352 may be in series with either the active valve 319 (and the pump 320-1) or the pump 320-2 (and the active valve 318).

The active valve 348, the pump 320-1, the active valve 318, the active valve 352, the active valve 318, and the pump 320-2 may be electronically controlled by a controller and/or driver (e.g., the controller 114 of FIG. 1, the controller 214 and the driver 236 of FIGS. 2A and 2B). The pump 320-1 and the pump 320-2 may be unidirectional or bidirectional. With respect to the fluid passageway 327, in some examples, the pump 320-1 and the active valve 319 may swap positions (e.g., where the active valve 319 is in series between the active valve 348 and the pump 320-1). With respect to the fluid passageway 324, in some examples, the active valve 318 and the pump 320-2 may swap positions (e.g., where the pump 320-1 is in series with and between the active valve 318 and the active valve 348).

In some examples, one or more additional active valves and/or one or more additional pumps are disposed in series within the fluid passageway 327. In some examples, one or more additional active valves and/or one or more additional pumps are disposed in series within the fluid passageway 324. In some examples, the electronic pump assembly 306 may include one or more additional (and parallel) fluid passageways, where each additional (and parallel) fluid passageway may include one or more active valves and one or more pumps.

In some examples, the electronic pump assembly 306 may include a pressure sensor 330 and a pressure sensor 331. The pressure sensor 330 and the pressure sensor 331 are connected to a controller (e.g., the controller 114 of FIG. 1, the controller 214 of FIGS. 2A and 2B), where the controller receives the measured pressure from the pressure sensor 330 and the pressure sensor 331.

The pressure sensor 330 is configured to measure the pressure in the inflatable member 304. The controller may receive the measured pressure from the pressure sensor 330 and automatically control the active valves and/or the pump to regulate the pressure. In some examples, the pressure sensor 331 is configured to measure the pressure in the fluid reservoir 302. In some examples, the pressure sensor 331 may detect intra-abdominal pressure (which can increase during activities such as exercise, and the controller can control the active valves and pump to minimize or prevent accidental inflations. In some examples, the electronic pump assembly 306 may include one or more pressure sensors at other locations within the electronic pump assembly 306. For example, a pressure sensor may be disposed between the active valve 348 and the pump 320-1. In some examples, a pressure sensor may be disposed between the pump 320-1 and the active valve 319. In some examples, a pressure sensor may be disposed between the active valve 348 and the active valve 318. In some examples, a pressure sensor may be disposed between the active valve 318 and the pump 320-2. In some examples, a pressure sensor may be placed between the inflatable member 304 and the active valve 352.

Figure 4:
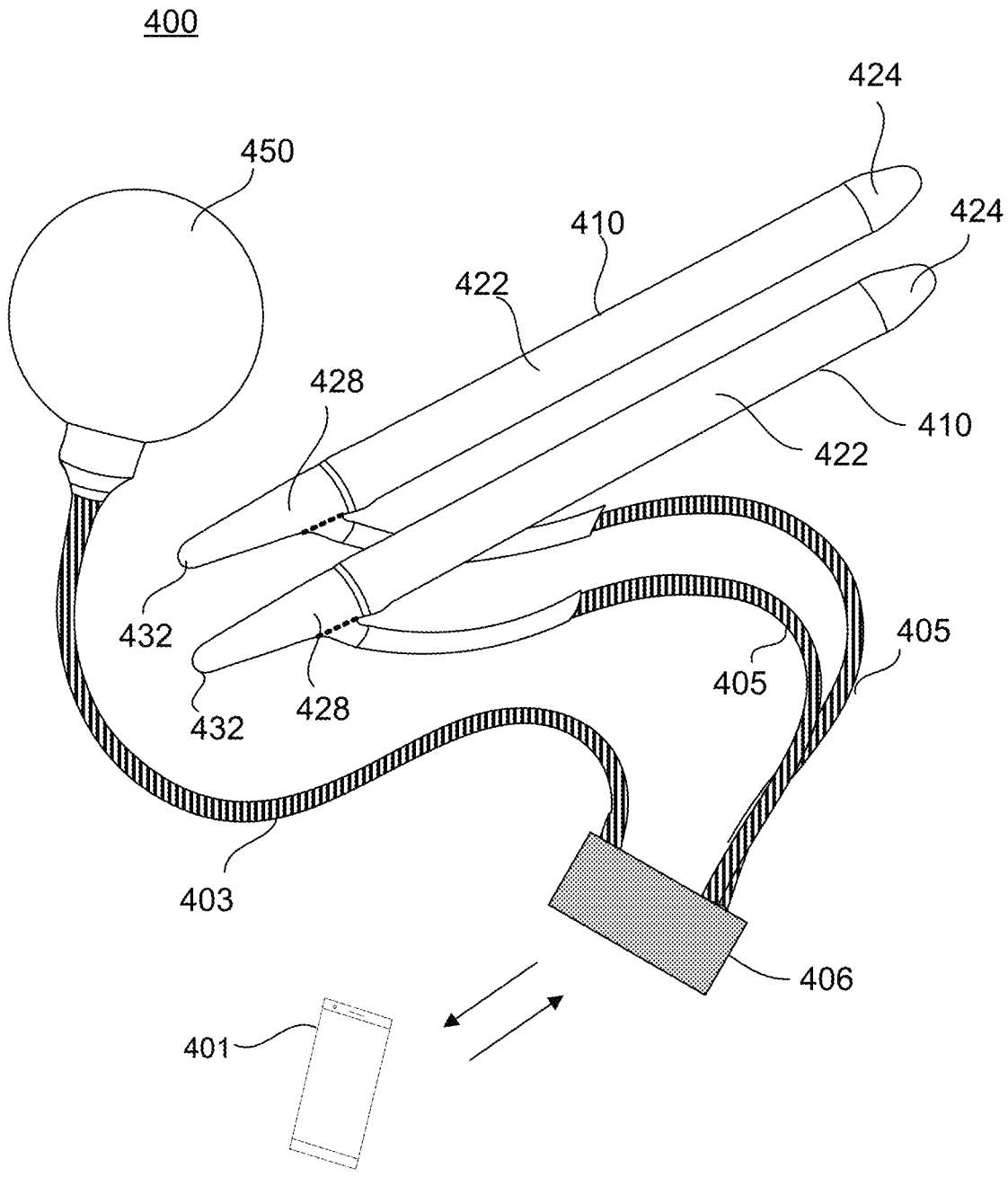
FIG. 4 illustrates an inflatable penile prosthesis having an electronic pump assembly according to another aspect.

FIG. 4 schematically illustrates an inflatable penile prosthesis 400 having an electronic pump assembly 406 according to an aspect. The electronic pump assembly 406 may include any of the features of the electronic pump assembly (e.g., 106, 206, 306) and the inflatable penile prostheses (e.g., 100, 200) discussed herein. The inflatable penile prosthesis 400 may include a pair of inflatable cylinders 410, and the inflatable cylinders 410 are configured to be implanted in a penis. For example, one of the inflatable cylinders 410 may be disposed on one side of the penis, and the other inflatable cylinder 410 may be disposed on the other side of the penis. Each inflatable cylinder 410 may include a first end portion 424, a cavity or inflation chamber 422, and a second end portion 428 having a rear tip 432.

At least a portion of the electronic pump assembly 406 may be implanted in the patient's body. A pair of conduit connectors 405 may attach the electronic pump assembly 406 to the inflatable cylinders 410 such that the electronic pump assembly 406 is in fluid communication with the inflatable cylinders 410. Also, the electronic pump assembly 406 may be in fluid communication with a fluid reservoir 450 via a conduit connector 403. The fluid reservoir 450 may be implanted into the user's abdomen. The inflation chamber 422 of the inflatable cylinder 410 may be disposed within the penis. The first end portion 424 of the inflatable cylinder 410 may be at least partially disposed within the crown portion of the penis. The second end portion 428 may be implanted into the patient's pubic region PR with the rear tip 432 proximate to the pubic bone PB.

In order to implant the inflatable cylinders 410, the surgeon first prepares the patient. The surgeon often makes an incision in the penoscrotal region, e.g., where the base of the penis meets with the top of the scrotum. From the penoscrotal incision, the surgeon may dilate the patient's corpus cavernosum to prepare the patient to receive the inflatable cylinders 410. The corpus cavernosum is one of two parallel columns of erectile tissue forming the dorsal part of the body of the penis, e.g., two slender columns that extend substantially the length of the penis. The surgeon will also dilate two regions of the pubic area to prepare the patient to receive the second end portion 428. The surgeon may measure the length of the corpora cavernosum from the incision and the dilated region of the pubic area to determine an appropriate size of the inflatable cylinders 410 to implant.

After the patient is prepared, the inflatable penile prosthesis 400 is implanted into the patient. The tip of the first end portion 424 of each inflatable cylinder 410 may be attached to a suture. The other end of the suture may be attached to a needle member (e.g., Keith needle). The needle member is inserted into the incision and into the dilated corpus cavernosum. The needle member is then forced through the crown of the penis. The surgeon tugs on the suture to pull the inflatable cylinder 410 into the corpus cavernosum. This is done for each inflatable cylinder 410 of the pair. Once the inflation chamber 422 is in place, the surgeon may remove the suture from the tip. The surgeon then inserts the second end portion 428. The surgeon inserts the rear end of the inflatable cylinder 410 into the incision and forces the second end portion 428 toward the pubic bone PB until each inflatable cylinder 410 is in place.

A user may use an external device 401 to control the inflatable penile prosthesis 400. In some examples, the user may use the external device 401 to inflate or deflate the inflatable cylinders 410. For example, in response to the user activating an inflation cycle using the external device 401, the external device 401 may transmit a wireless signal to the electronic pump assembly 406 to initiate the inflation cycle to transfer fluid from the fluid reservoir 450 to the inflatable cylinders 410. In some examples, in response to the user activating a deflation cycle using the external device 401, the external device 401 may transmit a wireless signal to the electronic pump assembly 406 to initiate the deflation cycle to transfer fluid from the inflatable cylinders 410 to the fluid reservoir 450. In some examples, during the deflation cycle, fluid is transferred back until the pressure in the inflatable cylinders 410 reaches a partial inflation pressure.

FIG. 5 illustrates a flow chart 500 depicting example operations of a method of operating an electronic pump assembly of an inflatable penile prosthesis. The example operations of the flow chart 500 may be performed by any of the inflatable penile prostheses (e.g., 100, 200, 400) and/or the electronic pump assemblies (e.g., 106, 206, 306, 406) discussed herein.

Operation 502 includes receiving, by an antenna of an electronic pump assembly, a wireless control signal from an external device. Operation 504 includes generating, by a controller, a first control signal to control an active valve of the electronic pump assembly. Operation 506 includes generating, by the controller, a second control signal to control a pump of the electronic pump assembly. Operation 508 includes actuating, in response to the first control signal, the active valve to a closed position. Operation 510 includes actuating, in response to the second control signal, the pump to transfer fluid from a fluid reservoir to an inflatable member until a pressure in the inflatable member reaches a threshold level. In some examples, the operations may include generating, by the controller, a third control signal to control the active valve. In some examples, the operations include actuating, in response to the third control signal, the active valve to an open position to transfer at least a portion of the fluid from the inflatable member to the fluid reservoir.

Detailed embodiments are disclosed herein. However, it is understood that the disclosed embodiments are merely examples, which may be embodied in various forms. Therefore, specific structural and functional details disclosed herein are not to be interpreted as limiting, but merely as a basis for the claims and as a representative basis for teaching one skilled in the art to variously employ the embodiments in virtually any appropriately detailed structure. Further, the terms and phrases used herein are not intended to be limiting, but to provide an understandable description of the present disclosure.

The terms "a" or "an," as used herein, are defined as one or more than one. The term "another," as used herein, is defined as at least a second or more. The terms "including" and/or "having", as used herein, are defined as comprising (i.e., open transition). The term "coupled" or "moveably coupled," as used herein, is defined as connected, although not necessarily directly and mechanically.

In general, the embodiments are directed to bodily implants. The term patient or user may hereafter be used for a person who benefits from the medical device or the methods disclosed in the present disclosure. For example, the patient can be a person whose body is implanted with the medical device or the method disclosed for operating the medical device by the present disclosure. For example, in some embodiments, the patient may be a human.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. An inflatable penile prosthesis comprising:
a fluid reservoir configured to hold fluid;
   an inflatable member; and
   an electronic pump assembly configured to transfer the fluid between the fluid reservoir and the inflatable member, the electronic pump assembly including:
a pump;
an active valve disposed in parallel with the pump;
a controller configured to control the pump and the active valve; and a hermetic enclosure, the hermetic enclosure including a hermetic fluid chamber, the hermetic fluid chamber, the controller being included within the hermetic enclosure but outside of the hermetic fluid chamber.

2. The inflatable penile prosthesis of claim 1, wherein the pump includes an electromagnetic pump.

3. The inflatable penile prosthesis of claim 1, wherein the pump includes a piezoelectric pump.

4. The inflatable penile prosthesis of claim 1, wherein the electronic pump assembly includes an antenna configured to receive a wireless control signal from an external device, the controller configured to control at least one of the pump or the active valve based on the wireless control signal.

5. The inflatable penile prosthesis of claim 1, wherein the pump is a first pump, the electronic pump assembly including a second pump.

6. The inflatable penile prosthesis of claim 5, wherein the second pump is disposed in parallel with the first pump.

7. The inflatable penile prosthesis of claim 6, wherein the second pump is configured to operate out of phase from the first pump.

8. The inflatable penile prosthesis of claim 5, wherein the second pump is disposed in series with the first pump.

9. The inflatable penile prosthesis of claim 1, wherein the pump includes one or more passive check valves.

10. An inflatable penile prosthesis comprising:
a fluid reservoir configured to hold fluid;
   an inflatable member; and
   an electronic pump assembly configured to transfer the fluid between the fluid reservoir and the inflatable member, the electronic pump assembly including:
a first pump;
a second pump;
an active valve;
a controller configured to control the first pump, the second pump, and the active valve; and
a hermetic enclosure, the hermetic enclosure including a hermetic fluid chamber, the hermetic fluid chamber including the first pump, the second pump, and the active valve, the controller being included within the hermetic enclosure but outside of the hermetic fluid chamber.

11. The inflatable penile prosthesis of claim 10, wherein the first pump and the active valve are in parallel with each other.

12. The inflatable penile prosthesis of claim 10, wherein the active valve is configured to transition between an open position in which the fluid flows through the active valve and a closed position in which the fluid is prevented from flowing through the active valve.

13. The inflatable penile prosthesis of claim 10, wherein the electronic pump assembly includes a pressure sensor, the controller configured to control at least one of the first pump, the second pump, or the active valve based on a pressure measured by the pressure sensor.

14. The inflatable penile prosthesis of claim 13, wherein the pressure sensor is connected to the inflatable member.

15. The inflatable penile prosthesis of claim 13, wherein the pressure sensor is connected to the fluid reservoir.

16. The inflatable penile prosthesis of claim 10, wherein the active valve is a first active valve, the electronic pump assembly including a second active valve.

17. The inflatable penile prosthesis of claim 16, wherein the second active valve is disposed in series with the first pump.

18. A method of operating an inflatable penile prosthesis, the method comprising:

receiving, by an antenna of an electronic pump assembly, a wireless control signal from an external device;

generating, by a controller disposed within a hermetic enclosure having a hermetic fluid chamber, a first control signal to control an active valve of the electronic pump assembly;

generating, by the controller, a second control signal to control a pump of the electronic pump assembly;

actuating, in response to the first control signal, the active valve to a closed position; and actuating, in response to the second control signal, the pump to transfer fluid from a fluid reservoir to an inflatable member until a pressure in the inflatable member reaches a threshold level.

19. The method of claim 18, further comprising:

generating, by the controller, a third control signal to control the active valve; and actuating, in response to the third control signal, the active valve to an open position to transfer at least a portion of the fluid from the inflatable member to the fluid reservoir.

\*　　\*　　\*　　\*　　\*